United States Patent [19]

Lavanish

[11] 4,156,602

[45] May 29, 1979

[54] 1-(1-CHLOROPROPYL)-2,4,6-TRIISOPROPYLBENZENE AND ITS USE TO CONTROL WEEDS

[75] Inventor: Jerome M. Lavanish, Akron, Ohio

[73] Assignee: PPG Industries, Inc., Pittsburgh, Pa.

[21] Appl. No.: 811,660

[22] Filed: Jun. 30, 1977

[51] Int. Cl.$^2$ .......................... A01N 9/30; C07C 25/14
[52] U.S. Cl. .................................. 71/126; 260/651 R
[58] Field of Search ....................... 71/126; 260/651 R

[56] References Cited

U.S. PATENT DOCUMENTS

| | | | |
|---|---|---|---|
| 2,998,460 | 8/1961 | Olah et al. | 71/126 |
| 3,373,011 | 3/1968 | Mussell | 71/126 |
| 3,879,191 | 4/1975 | Lavanish | 71/122 |
| 3,879,476 | 4/1975 | Deli et al. | 260/618 D |
| 3,911,029 | 10/1975 | Lavanish | 260/618 R |

OTHER PUBLICATIONS

Adams et al Editor, Organic Reactions, vol. 1, (1942) pp. 68–69.

*Primary Examiner*—Catherine L. Mills
*Attorney, Agent, or Firm*—Robert J. Grassi

[57] ABSTRACT

Disclosed are 1-(1-chloropropyl)-2,4,6-triisopropylbenzene and the method of controlling weeds, particularly crabgrass, by preemergent application of the compound to the soil.

9 Claims, No Drawings

1-(1-CHLOROPROPYL)-2,4,6-TRIISOPROPYL-BENZENE AND ITS USE TO CONTROL WEEDS

BACKGROUND OF THE INVENTION

1. Field of the Invention

This invention relates to triisopropylbenzyl chlorides, particularly 1-(1-chloropropyl)-2,4,6-triisopropylbenzene, and the method of controlling weeds, particularly crabgrass, by preemergent application of the compound to the soil.

2. Description of the Prior Art

The prior art is silent concerning 1-(1-chloropropyl)-2,4,6-triisopropylbenzene and the method of controlling weeds by preemergent application of the compound. For example, U.S. Pat. No. 2,430,822 describes the process for chlorinating isopropylbenzenes, a typical composition being hexachlorodiisopropylbenzene with a chlorine atom attached to each side chain carbon atom. U.S. Pat. No. 2,477,978 describes 3,4-dichloro-1-(α-chloro-β-trichloroethyl)-benzene, as being useful as a contact stomach or respiratory poison for insects. U.S. Pat. No. 2,573,394 describes a process for manufacturing chlorinated derivatives of α-chloroethylbenzene, which results in forming compounds such as α-chloroethylbenzene, α-chloroethylmonochlorobenzene, α-chloroethyl dichlorobenzene, α-chloroethyl trichlorobenzene, and α-chloroethyl trichlorostyrene. U.S. Pat. No. 2,794,054 describes alkyl α-chloromethylbenzhydrol ethers, and their use as miticides. U.S. Pat. No. 2,996,554 describes a process for making aryl substituted olefins from α-haloalkyl aryl compounds, such as α-chloroethyl isopropylbenzene, and α-chloro N-propylbenzene. U.S. Pat. No. 3,373,011 describes the method of suppressing plant growth with compositions of styrene, in which the phenyl group is substituted with alkyls or chlorines and a chloro substituted ethyl group is attached to the α-carbon of the styrene group, such as α-(2,2,2-trichloroethyl)styrene. U.S. Pat. No. 3,513,197 describes controlling algae with a 3-benzyl isothiuronium salt, which is made from a benzyl substituted with 1 to 3 alkyls or chlorine groups. U.S. Pat. No. 3,530,192 describes the synthesis of polychlorobenzyl chloride which is made from a chlorobenzyl such as 6-chloro-2-nitrotoluene. U.S. Pat. No. 3,877,927 describes substituted cyanobenzene acetonitriles and their halo-benzylhalide intermediates, such as 3-bromo-2,5-dichloro-4,6-diisopropylbenzyl chloride, as being effective for preemergent and post-emergent herbicides. U.S. Pat. No. 3,879,476 describes a method of preventing the establishment of weeds in the soil by the application of chlorinated benzyl alcohols such as 1-ethyl-2',4',6'-triisopropylbenzyl alcohol. U.S. Pat. No. 2,971,986 describes the method of preparing p-isopropyl-α-methylbenzyl alcohol. R. C. Fuson and C. H. McKeever, Organic Reactions, Vol. 1, R. Adams et al, Editor, Wiley, NY (1942), pages 68–69, discloses the compound 1-(chloromethyl)-2,4,6-triisopropylbenzene.

SUMMARY OF THE INVENTION

The invention concerns a novel composition, 1-(1-chloropropyl)-2,4,6-triisopropylbenzene, which may also be referred to as 1-ethyl-2',4',6'-triisopropylbenzyl chloride. The invention also concerns the method of controlling weeds of the genera Digitaria, Echinochloa, Sorghum, and Brassica, particularly the species *Digitaria sanguinalis* (L.) Scop., *Echinochloa crusgalli* (L.) Beauv., *Sorghum halepensis* (L.) Pers., and *Brassica kaber* (D.C.) L. C. Wheeler by preemergent application of the novel composition to the soil.

DESCRIPTION OF THE PREFERRED EMBODIMENTS

The composition of this invention is referred to here and in the claims as 1-(1-chloropropyl)-2,4,6-triisopropylbenzene, which term covers all of the optical steroisomers of the particular compound. This compound, in all of its optical steroisomer forms, may also be referred to as 1-ethyl-2',4',6'-triisopropylbenzyl chloride, and may be represented by the graphic structural formula:

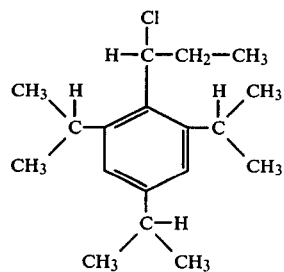

SYNTHESIS OF THE COMPOSITION

EXAMPLE I

Synthesis of 1-(1-Chloropropyl)-2,4,6-Triisopropylbenzene

A 100 milliliter flask was equipped with a magnetic stirrer and a pressure equalized addition funnel/drying tube. The flask was filled with a solution containing 50 milliliters of hexane and 15 grams (0.057 mole) of 1-(1-hydroxypropyl)-2,4,6-triisopropylbenzene (1-ethyl-2',4',6'-triisopropylbenzyl alcohol). The addition funnel was filled with a solution containing 10 milliliters of hexane and 8.9 grams (0.075 mole) of thionyl chloride. The solution of the thionyl chloride was slowly added to the solution of the 1-ethyl-2',4',6'-triisopropylbenzyl alcohol over a 45 minute period while stirring the reaction mixture. During the addition there was vigorous gas evolution, and after the addition the reaction mixture was left standing over night and then was cooled in an ice bath. After the reaction mixture was cooled, about 20 milliliters of ice water was rapidly added with stirring. After warming the reaction mixture to room temperature, the organic phase and water phase were separated, and the organic phase was washed with 5 portions of 20 milliliters of water, and then with a 20 milliliter solution of saturated sodium chloride. Then the organic phase was dried over magnesium sulfate and filtered. The solvent was evaporated from the organic phase using a rotary evaporator, to give 14.0 grams (92 percent) of a pale yellow liquid of the composition 1-(1-chloropropyl)-2,4,6-triisopropylbenzene.

The Analysis Calculated For: $C_{18}H_{29}Cl$: C, 76.8; H, 10.4; and Cl, 12.6 Found: C, 77.1; H, 10.5; and Cl, 12.9.

EXAMPLE II

Synthesis of 1-(chloromethyl)-2,4,6-Triisopropylbenzene

The known compound 1-(chloromethyl)-2,4,6-triisopropylbenzene was synthesized according to the method described by R. C. Fuson and C. H. McKeever,

*Organic Reactions,* Vol. 1, R. Adams et al, Editor, Wiley, NY (1942), pages 68-69.

The procedure for making the composition given in Example I is not limited to the use of hexane as a solvent but any solvent in which the 1-ethyl-2',4',6'-triisopropylbenzyl alcohol and the thionyl chloride are able to dissolve may be used in place of hexane. Furthermore, the temperature of the reaction mixture may vary from 10° C. to 70° C., but preferably it is around 15° C. to 20° C. The method of separating the composition from the solvent may be any standard method, such as crystallization, the addition of other solvents, such as alcohol, alkyl aliphatics of up to 15 chains, etc., which normally causes precipitation of the composition.

APPLICATION

The above described composition of 1-(1-chloropropyl)-2,4,6-triisopropylbenzene (1-ethyl-2',4',6'-triisopropylbenzyl chloride) may be formulated upon inert granules such as clay, silica gel, etc., or it may be dissolved in solvents and sprayed, or it may be combined with other agricultural formulations which are compatible with the composition such as the ureas, thiolcarbamates, or the isothiazolyl ureas, so as to produce a formulation which is not only nerbicidally effective against the weeds described herein, but also those weeds and plant pests which the other ingredients of the formulation are known to control.

Although the amount of compound to be applied will depend upon the environmental conditions, such as the nature of the soil, the weed species present, the weather, whether it be rainy, hot, or cold, the amount of the composition of 1-(1-chloropropyl)-2,4,6-triisopropylbenzene to apply will normally vary from about 2 pounds per acre to 50 pounds per acre. For general use, the amount will be from about 3 pounds per acre to 25 pounds per acre. It is preferred though, that from about 4 pounds per acre to about 15 pounds per acre be used, but most preferably 10 pounds per acre is used. Of course, depending upon the environmental conditions, one may apply as little as 1 pound per acre or even less than that in a series of applications, such as applying 1 pound per acre followed by another pound per acre, within a time period ranging from one to several days, or a week later. Normally the amount to apply, as used herein and in the claims, is that amount which is sufficient to prevent the establishment of the weed in the soil.

As used herein and in the claims, the term "weeds" refers to any undesirable plant species.

As used herein and in the claims, the phrase "applied preemergent to the soil" means preemergent to the weed, that is prior to the weed emerging from the soil. The amount applied preemergent to the soil is that which is sufficient to prevent the establishment of said weed in the soil. The range of that amount varies as mentioned herein, but most preferably it is ten (10) pounds per acre.

The weeds controlled by this preemergent application are broadleaf, grassy weeds, or mixtures thereof, particularly those of the genera Digitaria, Echinochloa, Sorghum, and Brassica; especially the weed species *Digitaria sanguinalis* (L.) Scop. (large crabgrass), *Echinochloa crusgalli* (L.) Beauv. (barnyardgrass), *Sorghum halepensis* (L.) Pers. (johnsongrass), and *Brassica kaber* (D.C.) L. C. Wheeler (wild mustard), or mixtures thereof. It is preferably used against weeds of the genus Digitaria, particularly the species *Digitaria sanguinalis* (L.) Scop. (large crabgrass). The other genus which it is preferably used against is that of Echinochloa, particularly the species *Echinochloa crusgalli* (L.) Beauv. (barnyardgrass).

The following test examples illustrate the use of the composition of 1-(1-chloropropyl)-2,4,6-triisopropylbenzene to control the weeds mentioned above.

EXAMPLE III

The composition of 1-(1-chloropropyl)-2,4,6-triisopropylbenzene from the synthesis described in Example I, was formulated in a solvent mixture (90 percent acetone, 8 percent methanol, and 2 percent dimethyl formamide by volume) to form a sprayable solution. The appropriate weed species were seeded in individual disposable, 3 inch square containers, containing about 2 inches of fertilized loam soil. A small amount of sand, usually $\frac{1}{8}$ to $\frac{1}{4}$ inch in depth, was applied to cover the seeds. Each container contained seeds of one species of weeds. The containers were placed on carrying trays and the carrying trays of containers were then positioned on a conveyor belt having a linear speed of 1.3 miles per hour, which passed through a spraying unit. As each tray moved along the conveyor belt, it tripped a microswitch which activated a solenoid valve to release the solution of the composition so as to spray it at the rate of 50 gallons per acre.

After the containers are sprayed with a solution of the composition, they were immediately removed and were watered so as to water in the composition and the containers were placed in a greenhouse and held for observation. Observations are made daily for an interim response, and the final observation was made at the conclusion of the holding period. Any treatments inducing especially significant responses were held beyond the regular holding period of two (2) weeks. The test results were reported according to the Injury Rating of: zero (0)—no visible effect, that is the weeds were not affected; 1, 2, or 3—slight injury, the plant usually recovered with little or no reduction in its top growth; 4, 5, or 6—moderate injury, the plants usually recovered but with reduced top growth; 7, 8, or 9—severe injury, the plants usually did not recover, or if they did, they were severely dwarfed in size; and 10—complete control, that is all weed species in the container were killed.

Using the above preemergent application procedure, the composition of 1-(1-chloropropyl)-2,4,6-triisopropylbenzene of Example I, was applied preemergent at 10 pounds per acre to seeds of the weed species *Digitaria sanguinalis* (L.) Scop. (large crabgrass) with the result that all weeds were killed, Injury Rating—10.

EXAMPLE IV

The known compound 1-(chloromethyl)-2,4,6-triisopropylbenzene from Example II, was applied according to the procedure described in Example III to large crabgrass (*Digitaria sanguinalis* (L.) Scop.), at 10 pounds per acre with the result that there was no control, that is the Injury Rating was zero (0).

EXAMPLE V

The composition from Example I of 1-(1-chloropropyl)-2,4,6-triisopropylbenzene was applied according to the procedure of Example III to the weed species *Echinochloa crusgalli* (L.) Beauv. (barnyardgrass) at 10 pounds per acre. The test results showed an Injury

EXAMPLE VI

When the composition from Example II of 1-(chloromethyl)-2,4,6-triisopropylbenzene was applied according to the procedure shown in Example III, against the species *Echinochloa crusgalli* (L.) Beauv. (barnyardgrass). The Injury Rating results were zero (0) control, meaning the plants were not visibly affected.

EXAMPLE VII

When the novel composition of Example I was applied according to the procedure of Example III, at 10 pounds per acre against the weed species *Brassica kaber* (D.C.) L. C. Wheeler (wild mustard), the test results gave an Injury Rating of 8. Those plants that survived showed necrosis and chlorosis.

EXAMPLE VIII

When the known composition of 1-(chloromethyl)-2,4,6-triisopropylbenzene of Example II was applied according to the procedure of Example III, at 10 pounds per acre against the weed species *Brassica kaber* (D.C.) L. C. Wheeler (wild mustard), the test results indicated zero (0), that is the plants were not visibly affected.

EXAMPLE IX

When the novel composition of Example I was applied according to the procedure of Example III at 10 pounds per acre against the weed species *Sorghum halepensis* (L.) Pers. (johnsongrass), the test results had an Injury Rating of 9, that is the plants were severely injured. Rating of 9. The dwarfed surviving plants also showed chlorosis.

EXAMPLE X

When the known composition of 1-(chloromethyl)-2,4,6-triisopropylbenzene of Example II was applied at 10 pounds per acre, according to the procedure of Example III, against the weed species *Sorghum halepensis* (L.) Pers. (johnsongrass), the test results indicated an Injury Rating of zero (0), that is there was no visible affect upon the plants.

While the invention has been described with reference to specific details of certain illustrative embodiments, it is not intended that it shall be limited thereby, except insofar as such details appear in the accompanying claims.

I claim:

1. 1-(1-chloropropyl)-2,4,6-triisopropylbenzene.

2. A method of controlling weeds which comprises:
   applying preemergent to the soil a composition comprised of 1-(1-chloropropyl)-2,4,6-triisopropylbenzene in an amount sufficient to prevent the establishment of said weed in the soil.

3. The method of claim 2, wherein the weed is selected from the group consisting of broadleaf weeds and grassy weeds.

4. The method as recited in claim 2, wherein the weeds are selected from the genera group consisting of Digitaria, Echinochloa, Sorghum, Brassica, or mixtures thereof.

5. The method of claim 2, wherein the weed is a species selected from the group consisting of *Digitaria sanguinalis* (L.) Scop., *Echinochloa crusgalli* (L.) Beauv., *Sorghum halepensis* (L.) Pers., *Brassica kaber* (D.C.) L. C. Wheeler, and mixtures thereof.

6. The method of claim 2, wherein the weed is of the genus Echinochloa.

7. The method of claim 2, wherein the weed is of the species *Echinochloa crusgalli* (L.) Beauv.

8. The method of claim 2, wherein the weed is of the genus Digitaria.

9. The method of claim 2, wherein the weed is of the species *Digitaria sanguinalis* (L.) Scop.

* * * * *